United States Patent [19]

Kulle et al.

[11] 4,335,770

[45] Jun. 22, 1982

[54] ENTERAL FEEDING CONTAINER

[75] Inventors: Lee K. Kulle, Mundelein; Kenneth W. Larson, Libertyville, both of Ill.

[73] Assignee: Baxter Travenol Laboratories, Inc., Deerfield, Ill.

[21] Appl. No.: 195,156

[22] Filed: Oct. 8, 1980

[51] Int. Cl.$^{3}$ .................................. A61M 31/00

[52] U.S. Cl. .................................. 150/8

[58] Field of Search .................. 150/8, 2.7; 128/222, 128/214 D, DIG. 24; 220/355

[56] References Cited

U.S. PATENT DOCUMENTS

| | | | |
|---|---|---|---|
| 1,934,547 | 11/1933 | Little | 150/2.7 |
| 2,303,733 | 12/1942 | Freeman | 150/8 X |
| 2,595,877 | 5/1952 | Otano . | |
| 3,006,341 | 10/1961 | Poitras | 128/214 D |
| 3,108,732 | 10/1963 | Curie | 150/8 X |
| 3,307,752 | 3/1967 | Anderson | 215/100 A X |
| 3,415,299 | 12/1968 | Hinman | 150/8 |
| 3,641,999 | 2/1972 | Greene . | |
| 3,690,524 | 9/1972 | Haberhauer . | |
| 3,783,920 | 1/1974 | Weikert . | |
| 3,915,212 | 10/1975 | Bujan et al. | 150/8 |
| 3,977,563 | 8/1976 | Holt | 220/355 |
| 4,076,027 | 2/1978 | Koenig . | |
| 4,126,167 | 11/1978 | Smith et al. . | |
| 4,182,342 | 1/1980 | Smith . | |
| 4,187,893 | 2/1980 | Bujan . | |

*Primary Examiner*—Donald F. Norton

*Attorney, Agent, or Firm*—John P. Kirby, Jr.; Garrettson Ellis; Bradford R. L. Price

[57] ABSTRACT

An enteral feeding container having a relatively enlarged port and closure which is resistant to popping open upon dropping. The enteral container may have a tapered portion for improved accuracy of administration.

16 Claims, 5 Drawing Figures

FIG. 2
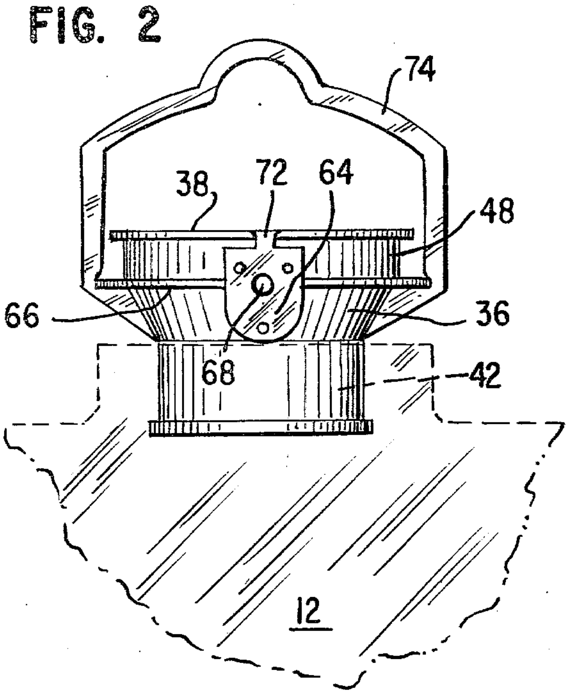
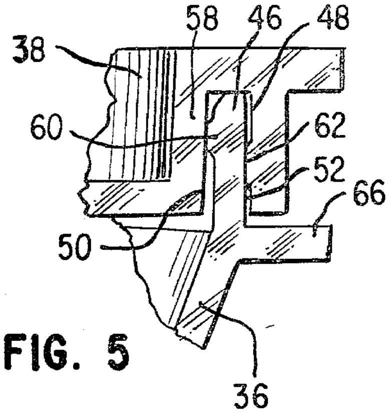
FIG. 5
FIG. 3
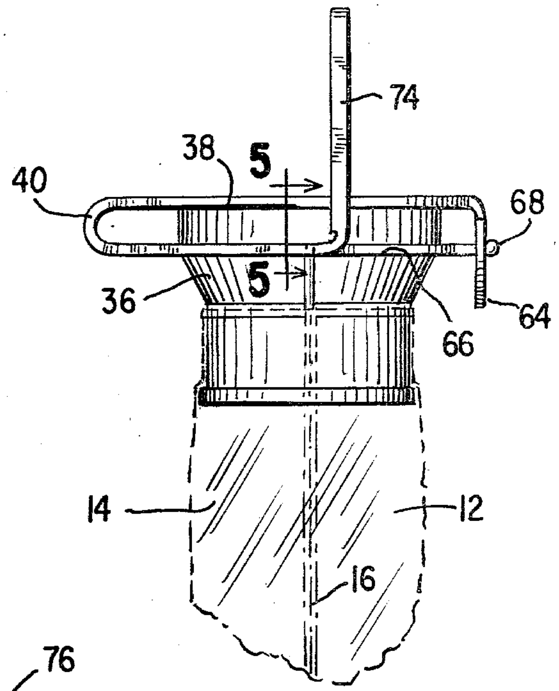
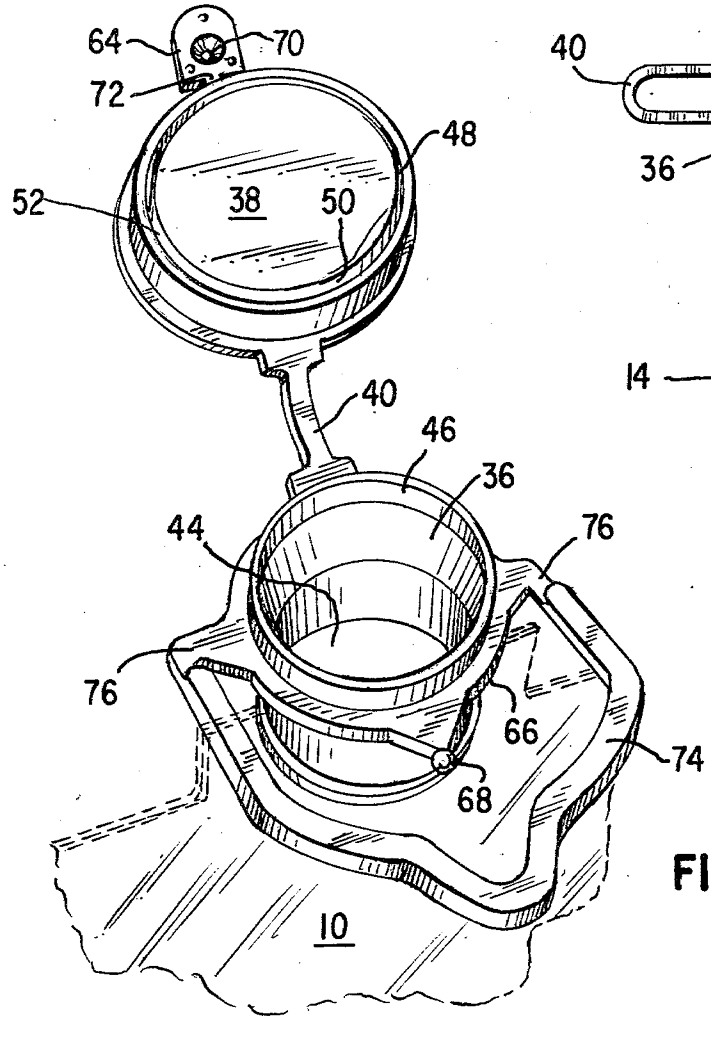
FIG. 4

ENTERAL FEEDING CONTAINER

TECHNICAL FIELD

The technique of enteral feeding of patients is growing in popularity, being a medical procedure for patients whose physical condition does not require intravenous feeding, but at the same time they are not yet prepared to take soft food or a liquid diet in normal manner. Furthermore, by means of enteral feeding a more complete diet can be provided than in many cases is available with parenteral solution administration or with soft food if the patient is, for example, a child who is an unwilling eater.

In enteral feeding, an enteral feeding catheter, for example a nasogastric tube, may communicate through the patient's nasal passage and extend all the way to the stomach. An enteral feeding container is connected to the outer end of the nasogastric tube, and the liquid food contents are directly conveyed to the stomach.

BACKGROUND ART

While enteral feeding containers are at the present time commercially available, for example the Hedeco Nutrifeed unit, there is a need for an enteral feeding container with a simple yet reliable large diameter inlet, for ease of insertion of the liquid nutrient into the container. At the same time, the closure of the inlet port must be leakproof and highly reliable, so that if the container is dropped during use the closure will not pop open. At the same time the container closure must be simple and inexpensive, since it is generally preferable for the enteral feeding container to be disposed of after a single use.

While it is well known and generally desirable to use polyvinyl chloride plastic containers because of their good flexibility, low expense and other good properties, it has proven difficult to make the large diameter port and closure out of polyvinyl chloride. For one reason, an inexpensive, one-piece polyvinyl chloride closure assembly has sufficiently low tensile strength that it has been difficult to formulate a good, molded hanger member connected in integral manner thereto, since the hanger tends to yield with the substantial weight of a filled central feeding container which may contain about 1.3 liters of solution, for example. Also at elevated storage temperatures, certain polyvinyl chloride closures have tended to seal together, making them very difficult to open.

On the other hand, many known plastic materials from which inlet closure ports might be made from are not easily sealed to polyvinyl chloride, so that common materials such as polyethylene or polypropylene cannot be easily used to make molded port and closure assemblies for a collapsible polyvinyl chloride enteral feeding container.

Furthermore, it is desirable for an enteral feeding container to have the capability of more precise measuring, then may be found in the prior art, of small amounts of liquified nutrient, for example up to 500 or 600 ml. of liquid, while at the same time providing a low cost, disposable container.

DISCLOSURE OF INVENTION

In accordance with this invention an enteral feeding container is provided. The term "enteral feeding" includes the idea of direct placement of nutrient into the stomach or bowel of a patient by means of an appropriate catheter or the like.

The enteral feeding container of this invention defines a pair of opposed, flexible, collapsible container walls, plus an outlet in the bottom of the container with the outlet communicating with flexible tubing which, in turn, terminates at its outer end with a connector for communication with an enteral feeding catheter.

An inlet port and closure is provided at the top of the container, having a diameter of at least 2 cm. and preferably somewhat larger, with the inlet port and closure comprising a funnel member sealed to the container walls and communicating therethrough. A closure member is attached to the funnel member by integral hinge means, with the funnel member defining an outwardly projecting cylindrical port.

The closure member defines outer and inner annular walls spaced apart to define an annular recess proportioned to receive in sealing relation the outwardly projecting cylindrical port of the funnel member when the closure is sealing the inlet port.

The inlet port and closure carry at least one annular sealing projection to press in sealing relation between the cylindrical port and annular walls when the inlet port and closure is in closed relation. The presence of one or more annular sealing projections of this type serves to provide firm retention of the closure member on the projecting cylindrical port of the funnel member to provide a leakproof seal. Also, the resistance to the container to opening its inlet port and closure upon dropping is greatly improved by the presence of one or more of such annular sealing projections.

Preferably, the annular sealing projection or projections which are present may preferably be from 0.008 to 0.025 cm. high. At least one of the annular sealing projections is preferably positioned on the inner surface of the cylindrical port, to press against the inner surface of the annular recess which receives the cylindrical port for sealing. Preferably, another annular sealing projection of the same height range as stated above may be positioned on the inner surface of the outer annular wall to form a pressure seal when the cylindrical port occupies the annular recess.

It is also preferable for the flexible container walls to be made of a polyvinyl chloride plastic, and the inlet port and closure to be of a single molded piece, connected by an integral hinge member, of a flexible block copolymer of covalently-bonded polybutylene terephthalate and poly(1,4-butylene) oxide units. Such a material is commercially available from E. I. duPont Nemours & Company under the tradename HYTREL. Typically, from 50 to 70 percent by weight of the block copolymer comprises 1,4-butylene oxide units. Such material has good sealing adhesion to polyvinyl chloride plastics and other desirable physical characteristics.

Furthermore, one of the funnel member and closure member may define a peripherally positioned, flexible, perforated lock tab, while the other of the funnel member and closure member defines an outwardly extending projection positioned and proportioned to fit through the perforated lock tab for locking the closure member in closed relation, to provide an extremely strong closure which cannot accidentally be opened even if the filled bag is dropped or stepped on, yet which is easily molded as an integral part of the one-piece funnel member and closure member.

Furthermore, the container of this invention may taper to a relatively narrow bottom so that the filled, tapered container portion is conical in shape, although it may be flat when empty. This provides an easy structure for accurate reading of the dispensing of relatively small amounts of solution up to 600 ml. for example, with accurate placement of liquid level indicia, for precise measurement of the administration of relatively small amounts of nutrient.

It is also often desirable for the inner surface of one of the container walls to be roughened to reduce container wall adhesion to each other.

BRIEF DESCRIPTION OF THE DRAWINGS

In the drawings,

FIG. 2 is a detailed fragmentary plan view of the closure member of the container of FIG. 1.

FIG. 3 is an elevational view similar to FIG. 2, but rotated 90° about its longitudinal axis.

FIG. 4 is a fragmentary perspective view of the closure of the container of this application, shown in its open position.

FIG. 5 is an enlarged sectional view taken along line 5—5 of FIG. 3.

DESCRIPTION OF SPECIFIC EMBODIMENT

Figure 1:
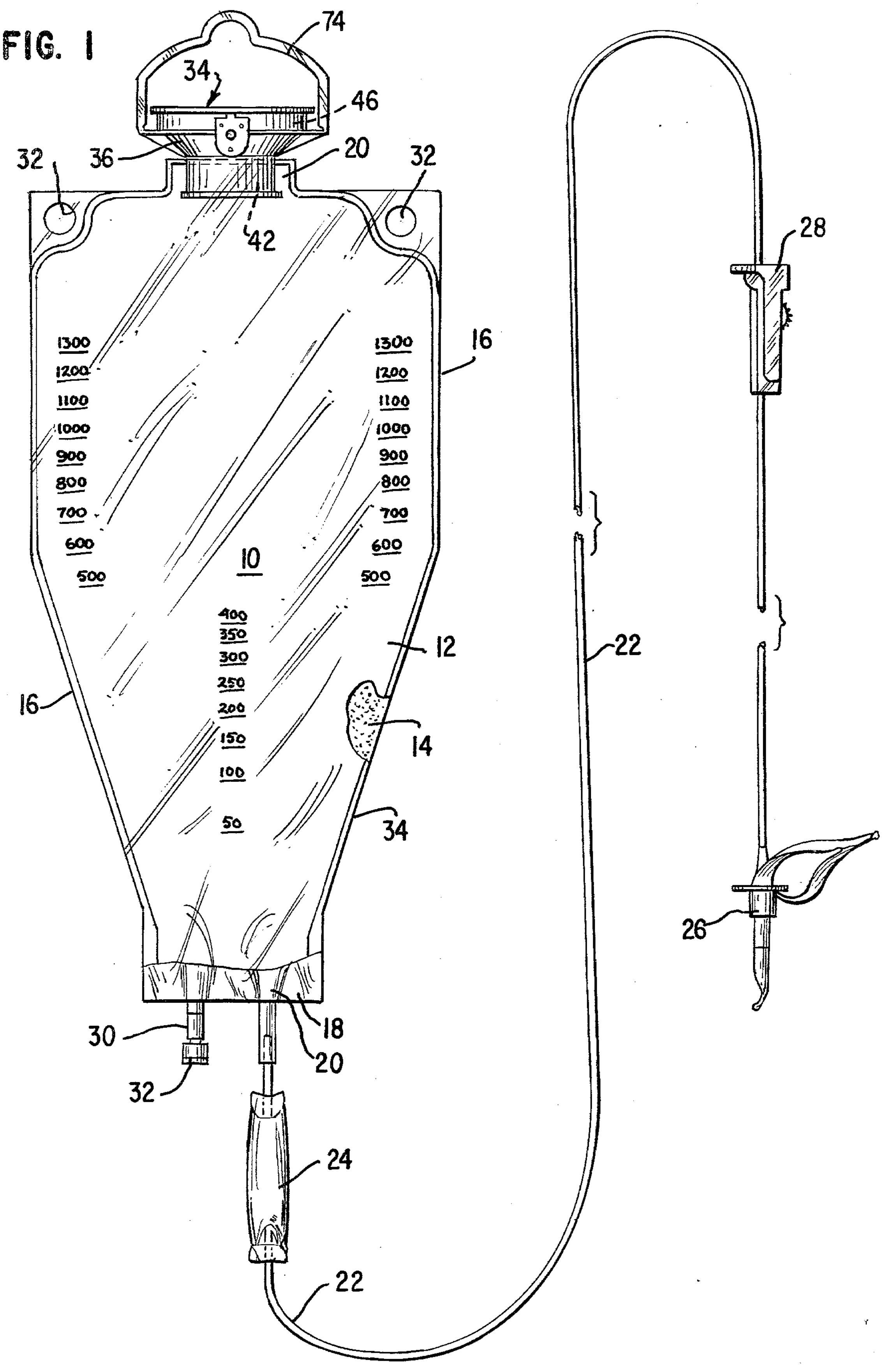
FIG. 1 is a plan view of the enteral feeding container of this invention, with a portion broken away.

Referring to the drawings, FIG. 1 shows enteral feeding container 10 which may be made of a pair of polyvinyl chloride sheets 12, 14 sealed together at their peripheries by a heat seal line 16, including end seals 18, 20, in the conventional manner of a heat-sealed plastic bag for solutions or the like.

The inner surface of plastic sheet 14 may have a matte or slightly roughened finish to reduce the adhesion of bag walls 12, 14 together, which makes the filling of bag 10 a more convenient and easy operation.

Container 10 carries an outlet 20 in its bottom which communicates with flexible tubing 22 through a conventional drip chamber 24. Tubing 22, in turn, communicates at its other end with a conventional connector 26, shown in this case to be a conventional luer type connector, for communication with an enteral feeding catheter such as a nasogastric catheter of known design which passes through the nasal passage of the patient and extends into or near the stomach.

Roller clamp 28 serves to control flow, while supplemental port 30, having a latex injection site 32 at its end, may be used for the addition of supplemental nutrients or medication as may be desired into container 10.

At the upper end of container 10, punch-through perforations 32 may be provided at a position outside of peripheral heat seal line 16 as shown.

Furthermore, as shown, container 10 may have a tapered portion 34 which forms a generally conical section of the container when filled. Because the tapered portion has less volume than an equivalent length of the larger section of container 10, the liquid level drops more upon the administration of a given amount of liquid contents. Volume indicia may be placed upon container 10 as shown, and the administration of small amounts of liquid, up to about 400 to 600 ml., can be carefully monitored, since in that circumstance the liquid level can lie within conical portion 34, which permits more detailed measurement. Also the regular geometric conical shape formed by section 34 provides further accuracy of administration, when compared with the accuracy of administration of simple rectangular, flexible bags and the like.

Inlet port and closure 34 of this invention comprises a funnel member 36 and a closure member 38 attached to the funnel member by integral hinge means 40, with funnel member 36, closure 38, and hinge means 40 being preferably all made out of a single molded piece of plastic, preferably the HYTREL plastic described above or equivalent material, particularly when the container walls 12, 14 are made of a polyvinyl chloride formulation, since such plastics are compatible with each other for heat sealing, while many other types of moldable plastics do not heat seal well with polyvinyl chloride compositions.

Funnel member 36 is hermetically heat sealed about neck portion 42 to each of sheets 12, 14, forming a part of heat sealed area 20 which extends in tight, hermetic relation about the outer periphery of neck portion 42. The heat sealed area 20 between bag walls 12, 14 and funnel member 36 may be formed by a conventional method.

Funnel member 36 is tubular in shape, and defines an aperture 44 communicating into the interior of bag 10 having a diameter of at least 2 cm. and preferably on the order of 3.5 to 5 cm. specifically about 3.8 cm. This provides an adequate aperture to pour in prepared liquid nutrient preparations.

Funnel member 36 also defines an outwardly projecting cylindrical port 46. Closure member 38 defines outer annular wall 48 and inner annular wall 50, which are spaced apart to define an annular recess 52, which is proportioned to sealingly receive the outwardly projecting cylindrical port 56 of funnel member 36, when the closure is sealing inlet port 44.

Annular sealing projections are provided to provide an annular pressure seal between cylindrical port 46 and, respectively, inner annular wall 58 and outer annular wall 48. Annular sealing projection 60 may be carried on the inner surface of cylindrical port 46 as shown, while annular sealing projection 62 may be carried on the inner surface of outer wall 48. However, the annular projections may be carried in the outer surfaces of inner annular wall 58 and cylindrical port 46 is desired, or, alternatively, only a single one of the annular sealing projections may be used if the closure is desired to be more easily removed. Annular sealing projection 60, 62 may have a height, relative to the surface from which they project, on the order of 0.0127 cm. (about 0.005 inch), with the height being adjusted to provide the desired sealing and closure retention results.

In actual experimentation relative to bags similar to the design of this present bag, it has been found that with the closure of this invention, in the absence of sealing projections 60, 62, but providing an adequate, tight fit of cylindrical port 46 in annular recess 52, containers filled with about 1300 ml. of liquid are usually not able to resist a 3 foot drop without opening, if there are no additional means for holding closure member 38 in its sealed position. With the addition of annular sealing projection 60, the filled containers of this invention can withstand a 6 foot drop 50 percent of the time without opening. With the addition of sealing projections 62, the filled containers of this invention can withstand a 6 foot drop more than 85 percent of the time.

Closure member 38 further defines a peripherally positioned flexible, perforated lock tab 64. Funnel member 36, in turn, defines a peripheral flange 66 which carries in one position an outwardly extending projection 68 which is positioned and proportioned to fit through perforation 60 of lock tab 64. Lock tab 64 is carried on a flexible hinge 72 so that funnel member 36 and closure 38 may be positively retained together in the closed position when that is desired. For this reason, the container of this invention can be roughly handled when it is in its fully-closed position, even though filled with liquid. It can be accidentally dropped or even stepped on without opening, when lock tab 64 is in its locking position. Lock tab 64 may be part of the integrally molded piece comprising funnel member 36 and closure member 38.

Hanging handle 74 may also be part of the integrally molded plastic piece including funnel member 36 and closure 38 with the handle in its as-molded condition being shown in FIG. 4. Thin hinge member 76 at the junction of handle 74 with flange 66 permits the bending of handle 74 upwardly as shown in FIGS. 1, 2 and 3 for hanging of the container on an IV pole.

Accordingly, liquid nutrients may be inserted into the open mouth 44 of funnel member 36 to fill the bag to the desired level. Closure 38 may then be sealed in the manner shown herein and locked with tab 64.

Luer connector 26 may be connected with a nasogastric catheter of a patient, and container 10 hung on an IV pole by means of hanger member 74. Thereafter, the flow of liquid nutrient may be controlled in conventional manner by roller clamp 28 to provide the patient with the desired nutrient in a convenient and aseptic manner.

The above has been offered for illustrative purposes only, and is not intended to limit the scope of this invention, which is as defined in the claims below.

That which is claimed is:

1. An enteral feeding container, which comprises a container body defined by a pair of opposed, flexible, collapsible container walls, an outlet in the bottom of said container, said outlet communicating with flexible tubing which terminates at its outer end with connector means for communication with an enteral feeding catheter, and an inlet port and closure at the top of said container having a diameter of at least 2 cm., said inlet port and closure comprising a funnel member sealed to said container walls and communicating therethrough, and a closure member attached to said funnel member by integral hinge means, said funnel member defining an outwardly projecting cylindrical port, said closure member defining outer and inner annular walls spaced apart to define an annular recess proportioned to sealingly receive said outwardly projecting cylindrical port when said closure is sealing the inlet port, said inlet port nd closure carrying at least one annular sealing projection for sealing between said cylindrical port and annular walls when the inlet port and closure is in closed relation.

2. The container of claim 1 in which an annular sealing projection, 0.008 to 0.025 cm. high, is positioned on the inner surface of said cylindrical port.

3. The container of claim 2 in which an annular sealing projection, 0.008 to 0.025 cm. high, is positioned on the inner surface of said outer annular wall.

4. The container of claim 1 in which said flexible container walls are made of polyvinyl chloride plastic, and said inlet port and closure comprises a single molded piece of a flexible block copolymer of covalently-bonded polybutylene terephthalate units and poly(1,4-butylene) oxide units.

5. The container of claim 4 in which 50 to 70 percent by weight of said block copolymer comprises 1,4-butylene oxide units.

6. The container of claim 1 in which one of said funnel member and closure member defines a peripherally positioned flexible, perforated lock tab, and the other of said funnel member and closure member defines an outwardly extending projection positioned and proportioned to fit through the perforated lock tab for locking the closure member in closed relation.

7. The container of claim 1 in which said inlet port and closure is a single molded piece of plastic, including integral, flexible hanger means.

8. The container of claim 1 in which said container tapers to relatively narrow bottom, whereby the filled, tapered container portion is conical in shape.

9. The container of claim 1 in which an inner surface of at least one of said container walls is roughened to reduce container wall adhesion.

10. An enteral feeding container which comprises a container body defined by a pair of opposed, flexible, collapsible container walls, an outlet in the bottom of said container, said outlet communicating with flexible tubing which terminates at its outer end with connector means for communication with an enteral feeding catheter, and an inlet port and closure at the top of said container, said port having a diameter of at least 2 cm., said inlet port and closure comprising a funnel member sealed to said container walls and communicating therethrough, and a closure member attached to said funnel member by integral hinge means, said funnel member defining an outwardly projecting cylindrical port, said closure member defining outer and inner annular walls spaced apart to define an annular recess proportioned to sealingly receive said outwardly projecting cylindrical port when said closure is sealing the inlet port, said inlet port and closure carrying annular sealing projections to seal the space between both sides of said cylindrical port and the respective annular walls when the inlet port and closure are in closed position, said flexible container walls being made of a polyvinyl chloride plastic, and said inlet port and closure being a single molded piece of a flexible block copolymer of covalently-bonded polybutylene terephthalate units and poly(1,4-butylene) oxide units.

11. The container of claim 10 in which the annular sealing projections on both sides of the cylindrical port are from 0.008 to 0.025 cm. high.

12. The container of claim 11 in which 50 to 70 percent by weight of said block copolymer comprises 1,4-butylene oxide units.

13. The container of claim 12 in which one of said funnel member and closure member defines a peripherally positioned, flexible, perforated lock tab, and the other of said funnel member and closure member defines an outwardly extending projection positioned and proportioned to fit through the perforated lock tab for locking the closure member in closed relation.

14. The container of claim 13 in which said inlet port and closure also includes integral flexible hanger means.

15. The container of claim 14 in which said container tapers to a relatively narrow bottom, whereby the filled, tapered container portion is conical in shape.

16. The container of claim 15 in which an inner surface of at least one of said container walls is roughened to reduce the container wall adhesion.

* * * * *